US012778627B2

(12) United States Patent
Glaspie et al.

(10) Patent No.: US 12,778,627 B2
(45) Date of Patent: Nov. 3, 2026

(54) IMPLANT AND SYSTEM TO FACILITATE ACCESS ACROSS PLEURA LAYERS

(71) Applicant: Bard Peripheral Vascular, Inc., Franklin Lakes, NJ (US)

(72) Inventors: Koltin Glaspie, Chandler, AZ (US); Heather Storm, Phoenix, AZ (US); Jordan Addison, Gilbert, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 1103 days.

(21) Appl. No.: 17/641,123

(22) PCT Filed: Sep. 16, 2019

(86) PCT No.: PCT/US2019/051287
§ 371 (c)(1),
(2) Date: Mar. 8, 2022

(87) PCT Pub. No.: WO2021/054932
PCT Pub. Date: Mar. 25, 2021

(65) Prior Publication Data

US 2023/0270465 A1 Aug. 31, 2023

(51) Int. Cl.
*A61B 17/34* (2006.01)

(52) U.S. Cl.
CPC ...... *A61B 17/3423* (2013.01); *A61B 17/3415* (2013.01); *A61B 2017/3427* (2013.01)

(58) Field of Classification Search
CPC ............ A61B 17/3423; A61B 17/3415; A61B 2017/3427; A61B 17/3417; A61M 25/0668
See application file for complete search history.

(56) References Cited

U.S. PATENT DOCUMENTS

| | | | | |
|---|---|---|---|---|
| 3,777,757 A | | 12/1973 | Gray et al. | |
| 4,740,207 A | * | 4/1988 | Kreamer | A61F 2/92 623/1.34 |
| 4,921,479 A | * | 5/1990 | Grayzel | A61M 25/0668 604/509 |
| 5,304,187 A | * | 4/1994 | Green | A61B 17/29 606/151 |
| 5,391,156 A | | 2/1995 | Hildwein et al. | |
| 5,562,677 A | | 10/1996 | Hildwein et al. | |
| 6,629,951 B2 | | 10/2003 | Laufer et al. | |

(Continued)

FOREIGN PATENT DOCUMENTS

WO 2019108618 A1 6/2016

*Primary Examiner* — Bhisma Mehta
*Assistant Examiner* — Fatimata Sahra Diop
(74) *Attorney, Agent, or Firm* — Dinsmore & Shohl LLP

(57) ABSTRACT

An implant device to facilitate access across pleura layers includes a tube having a side wall, a lumen, a proximal end portion, a distal end portion, and a central portion interposed between the proximal end portion and the distal end portion. The tube has a longitudinal extent, wherein each of the proximal end portion and the distal end portion extends outwardly from the central portion, and wherein the side wall has a longitudinal split to define a first lateral edge surface and a second lateral edge surface. Each of the first lateral edge surface and the second lateral edge surface longitudinally extends through each of the proximal end portion, the central portion, and the distal end portion.

18 Claims, 9 Drawing Sheets

(56) References Cited

U.S. PATENT DOCUMENTS

| | | | |
|---|---|---|---|
| 6,712,812 B2 | 3/2004 | Roschak et al. | |
| 7,175,644 B2 | 2/2007 | Cooper et al. | |
| 7,182,772 B2 * | 2/2007 | Alferness | A61B 17/12013 606/157 |
| 7,377,278 B2 | 5/2008 | Tanaka | |
| 7,422,584 B2 | 9/2008 | Loomas et al. | |
| 7,462,162 B2 | 12/2008 | Phan et al. | |
| 7,682,332 B2 | 3/2010 | Tanaka | |
| 7,708,712 B2 | 5/2010 | Phan et al. | |
| 7,811,274 B2 | 10/2010 | Tanaka et al. | |
| 7,815,590 B2 | 10/2010 | Cooper | |
| 8,002,740 B2 | 8/2011 | Willink et al. | |
| 8,163,034 B2 | 4/2012 | Chang et al. | |
| 8,220,460 B2 | 7/2012 | Tanaka | |
| 8,518,053 B2 | 8/2013 | Tanaka et al. | |
| 8,932,316 B2 | 1/2015 | Keast et al. | |
| 2006/0025815 A1 * | 2/2006 | McGurk | A61B 17/32002 600/564 |
| 2006/0280773 A1 * | 12/2006 | Roschak | A61B 17/064 424/426 |
| 2012/0053485 A1 | 3/2012 | Bloom | |
| 2013/0226026 A1 | 8/2013 | Dillard et al. | |
| 2013/0338646 A1 | 12/2013 | Butler et al. | |
| 2015/0057570 A1 | 2/2015 | Chin et al. | |
| 2015/0057742 A1 * | 2/2015 | Steckel | A61L 31/022 623/1.16 |
| 2019/0030286 A1 | 1/2019 | Mathis et al. | |
| 2019/0117949 A1 | 4/2019 | Waysbeyn et al. | |
| 2019/0167407 A1 | 6/2019 | Schaer et al. | |
| 2020/0360051 A1 * | 11/2020 | Bresnick | A61B 17/3431 |

* cited by examiner

IMPLANT AND SYSTEM TO FACILITATE ACCESS ACROSS PLEURA LAYERS

CROSS-REFERENCE TO RELATED APPLICATIONS

This application is a U.S. National Phase of International Application No. PCT/US2019/051287, entitled "IMPLANT AND SYSTEM TO FACILITATE ACCESS ACROSS PLEURA LAYERS" and filed Sep. 16, 2019, which is incorporated herein by reference in its entirety.

TECHNICAL FIELD

The present invention relates to a lung access procedure, such as a lung biopsy, and, more particularly, to an implant and system to facilitate access across pleura layers.

BACKGROUND ART

Pneumothorax is a problematic complication of the lung biopsy procedure where air or fluid is allowed to pass into the pleural space as a result of the puncture of the parietal pleura and visceral pleura. Pneumothorax and, more so, pneumothorax requiring chest tube placement, are significant concerns for clinicians performing, and patients undergoing, percutaneous lung biopsies. The incidence of pneumothorax in patients undergoing percutaneous lung biopsy has been reported to be anywhere from 9-54%, with an average of around 15%. On average, 6.6% of all percutaneous lung biopsies result in pneumothorax requiring a chest tube to be placed, which results in an average hospital stay of 2.7 days.

Factors that increase the risk of pneumothorax include increased patient age, obstructive lung disease, increased depth of a lesion, multiple pleural passes, increased time that an access needle lies across the pleura, and traversal of a fissure. Pneumothorax may occur during or immediately after the procedure, which is why typically a CT scan of the region is performed following removal of the needle. Other, less common, complications of percutaneous lung biopsy include hemoptysis (coughing up blood), hemothorax (a type of pleural effusion in which blood accumulates in the pleural cavity), infection, and air embolism.

What is needed in the art is an implant and system to facilitate access across pleura layers, which aids in the prevention of pneumothorax.

SUMMARY OF INVENTION

The present invention provides an implant and system to facilitate access across pleura layers, which aids in the prevention of pneumothorax.

The invention, in one form, is directed to an implant device to facilitate access across pleura layers. The implant includes a tube having a side wall, a lumen, a proximal end portion, a distal end portion, and a central portion interposed between the proximal end portion and the distal end portion. The tube has a longitudinal extent, wherein each of the proximal end portion and the distal end portion extends outwardly from the central portion. The side wall has a longitudinal split to define a first lateral edge surface and a second lateral edge surface. Each of the first lateral edge surface and the second lateral edge surface longitudinally extends through each of the proximal end portion, the central portion, and the distal end portion.

The invention, in another form, is directed to a system to facilitate access across pleura layers. The system includes an implantable tube, a stylet assembly, and a cannula assembly. The implantable tube has a tubular side wall, a tubular lumen, a proximal end portion, a distal end portion, and a central portion interposed between the proximal end portion and the distal end portion. The implantable tube has a longitudinal extent, wherein each of the proximal end portion and the distal end portion extends outwardly from the central portion. The tubular side wall has a longitudinal split to define a first lateral edge surface and a second lateral edge surface. Each of the first lateral edge surface and the second lateral edge surface longitudinally extends through each of the proximal end portion, the central portion, and the distal end portion. The stylet assembly has a stylet and a stylet handle. The stylet has a distal tip, and has an exterior surface and a longitudinal recess formed along the exterior surface. The longitudinal recess has a longitudinal edge surface. The tubular lumen of the implantable tube is configured to be received over the exterior surface of the elongate member, with the first lateral edge surface of the tubular side wall of the implantable tube configured to be engaged by the longitudinal edge surface of the longitudinal recess of the stylet. The cannula assembly has a cannula and a cannula handle. The cannula has a cannula side wall and a cannula lumen. The cannula side wall has a distal end and a longitudinal slotted opening proximal to the distal end. The implantable tube and at least a portion of the stylet are configured to be received in the cannula lumen, with the second lateral edge surface of the tubular side wall of the implantable tube configured to be received through the longitudinal slotted opening of the cannula side wall.

An advantage of the present invention is that the implant device facilitates access across pleura layers to aid in preventing pneumothorax, before, or coincident with, the performing of a lung biopsy.

BRIEF DESCRIPTION OF DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate several embodiments of the invention, and such exemplifications are not to be construed as limiting the scope of the invention in any manner.

DESCRIPTION OF EMBODIMENTS

Figure 1:
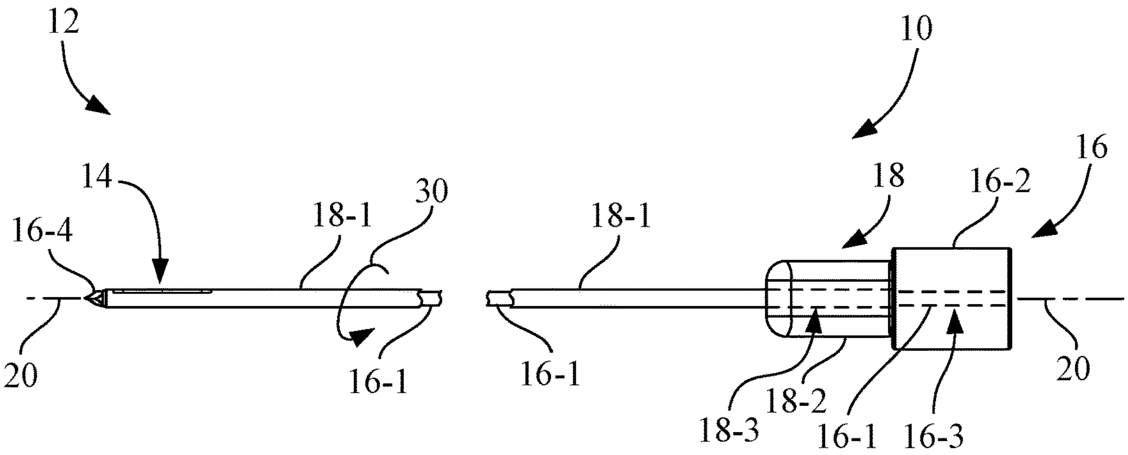
FIG. 1 is a side view of an implant system in a pre-deployment state, which includes an implant introducer device and an implant device that is carried by the implant introducer device, in accordance with an aspect of the present invention.

Referring now to the drawings, and more particularly to FIGS. 1-4, there is shown an implant system 10, which includes an implant introducer device 12 and an implant device 14 that is carried by implant introducer device 12. Implant system 10, including implant introducer device 12 and implant device 14, is configured to facilitate access across pleura layers of a patient.

Implant introducer device 12 includes a stylet assembly 16 and a cannula assembly 18. Stylet assembly 16 and cannula assembly 18 are arranged along a longitudinal axis 20, such that stylet assembly 16 and cannula assembly 18 are coaxial. Stylet assembly 16 and cannula assembly 18 are configured to rotate relative to each other around longitudinal axis 20, e.g., in opposite rotational directions, so to deploy, i.e., expel, the implant device 14 from cannula assembly 18. Rotational deployment allows implant device 14 to be pre-positioned longitudinally, prior to deployment.

Figure 3:
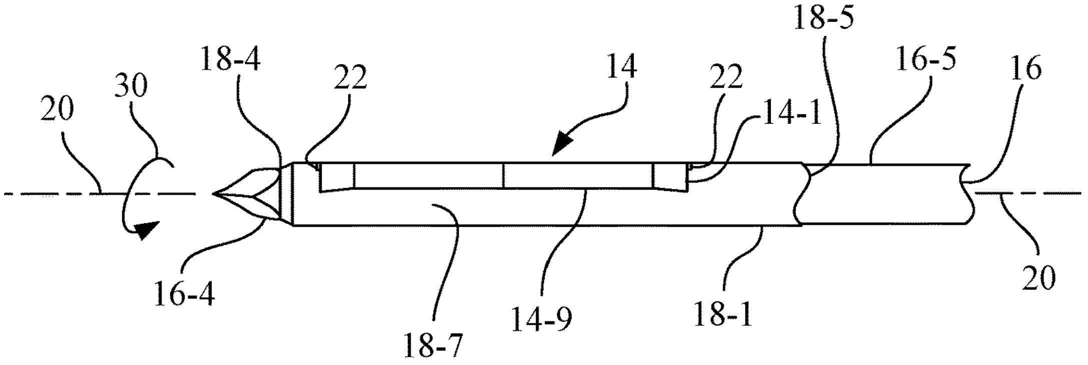
FIG. 3 is an enlarged view of the implant system of FIG. 2, during an implant device deployment state, with the implantable tube partially extending through the longitudinal slotted opening in the cannula of the implant introducer device.
Figure 4:
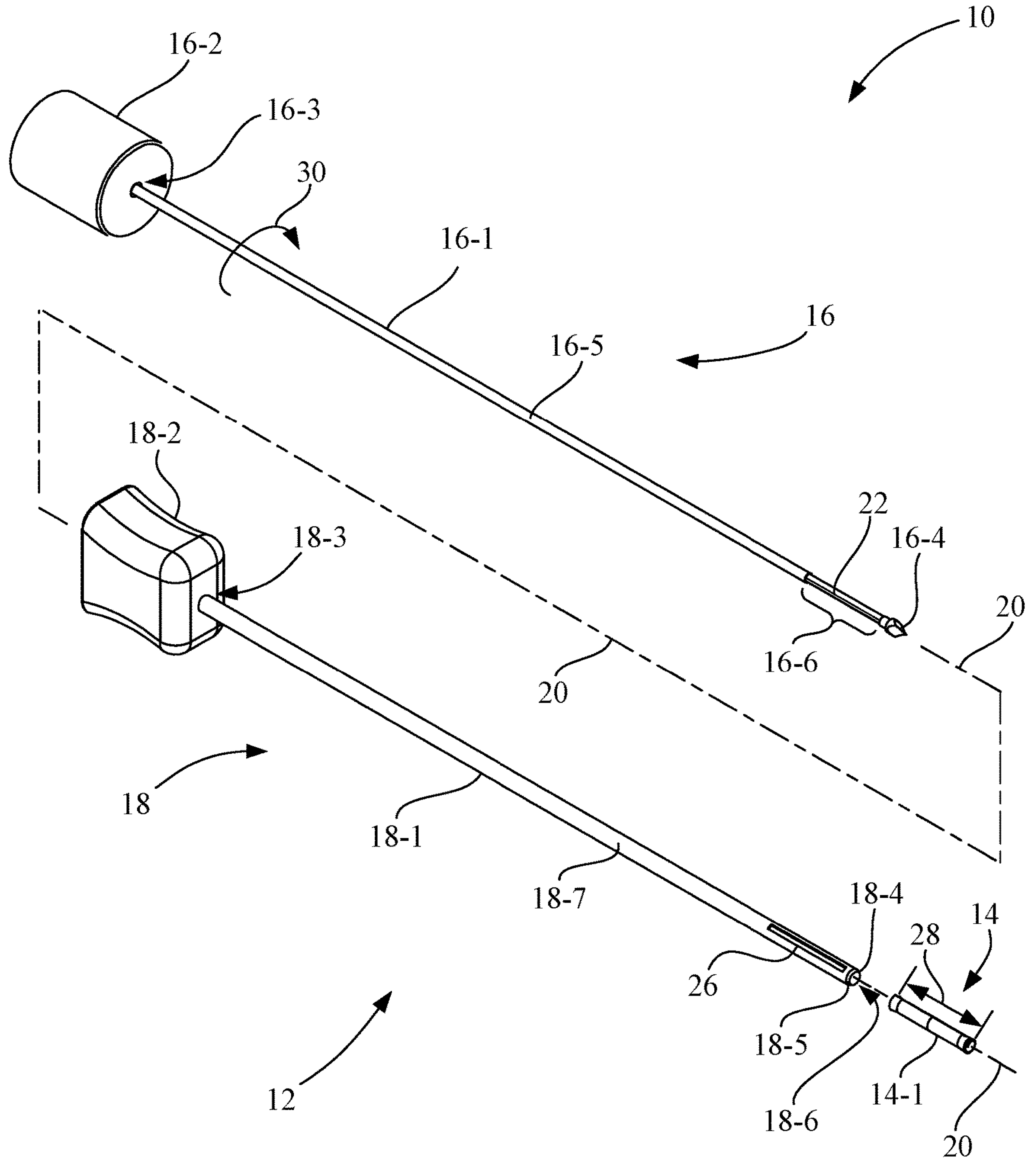
FIG. 4 is an exploded view of the implant introducer device and implant device of FIG. 1.

Referring to FIGS. 1 and 4, stylet assembly 16 includes a stylet 16-1 and a stylet handle 16-2. Referring to FIGS. 1-6, stylet 16-1 is in the form of an elongate shaft that has a proximal end portion 16-3 and a distal tip 16-4. Distal tip 16-4 defines a distal portion of stylet assembly 16. Stylet 16-1 may be, for example, either of a hollow shaft or a solid shaft. Distal tip 16-4 may be integral with stylet 16-1, or alternatively, may be fixedly connected to stylet 16-1. Stylet 16-1 of stylet assembly 16 has an exterior surface 16-5.

Stylet handle 16-2 is fixedly connected to proximal end portion 16-3 of stylet 16-1. The term "fixedly connected" means a coupling between two or more components wherein the respective components are not readily separated from each other. For example, the fixed connection of stylet handle 16-2 to stylet 16-1 may be achieved, for example, by adhesive, weld, press fit, or screw connection.

Figure 5:
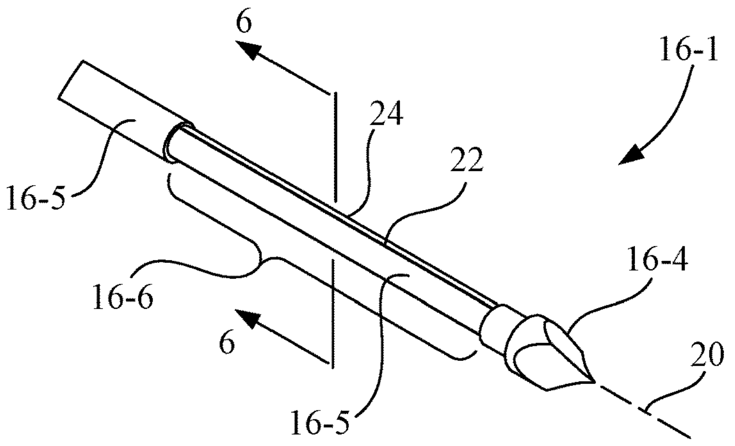
FIG. 5 is an enlarged view of a portion of the stylet of the implant introducer device of FIG. 4, showing a longitudinal edge surface used to rotate the implant device relative to the longitudinal slotted opening in the cannula shown in FIG. 3.
Figure 6:
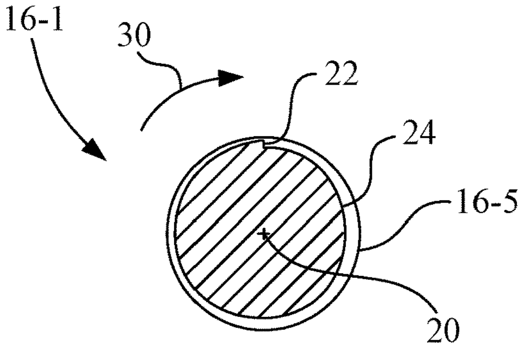
FIG. 6 is a section view of the stylet of FIG. 5.

Referring particularly to FIGS. 4 and 5, stylet 16-1 has a longitudinal recess 16-6. Longitudinal recess 16-6 is formed along exterior surface 16-5 of stylet 16-1, and may surround an entirety of a circumference of a longitudinal portion of stylet 16-1 of stylet assembly 16, as best shown in FIG. 5. Referring also to FIG. 6, longitudinal recess 16-6 includes a longitudinal edge surface 22 that may extend the full longitudinal length of longitudinal recess 16-6.

Referring to FIGS. 5 and 6, exterior surface 16-5 within longitudinal recess 16-6 has an outwardly spiral surface portion 24 around stylet 16-1 to define longitudinal edge surface 22. Stated differently, in a clockwise path around longitudinal recess 16-6, longitudinal edge surface 22 both begins and terminates outwardly spiral surface portion 24. In practice, longitudinal edge surface 22 forms a pushing surface when stylet 16-1 of stylet assembly 16 is rotated by rotating stylet handle 16-2 of stylet assembly 16.

Referring again to FIGS. 1 and 4, cannula assembly 18 includes a cannula 18-1 and a cannula handle 18-2. Referring to FIGS. 1-4 and 7, cannula 18-1 includes a proximal end portion 18-3, a distal end 18-4, a cannula side wall 18-5, a cannula lumen 18-6, and an outer surface 18-7. Cannula handle 18-2 is fixedly connected to proximal end portion 18-3 of cannula 18-1.

Figure 7:
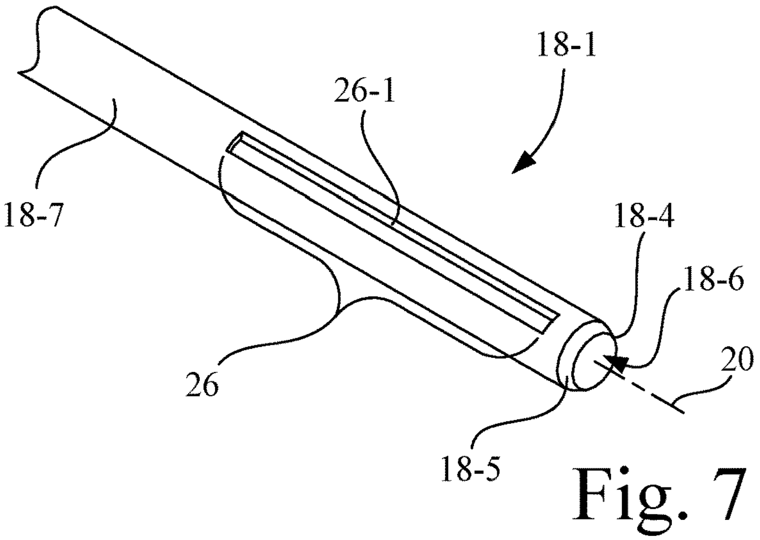
FIG. 7 is an enlarged view of a portion of the cannula of the implant introducer device of FIG. 4, showing the longitudinal slotted opening of the cannula.

Cannula side wall 18-5 includes distal end 18-4, and has a longitudinal slotted opening 26 that is proximal to distal end 18-4. As best shown in FIG. 7, longitudinal slotted opening 26 includes a ramp 26-1 that radially extends from cannula lumen 18-6 to outer surface 18-7 of the cannula 18-1, and may longitudinally extend the full longitudinal length of longitudinal slotted opening 26. Ramp 26-1 of longitudinal slotted opening 26 is configured to guide implant device 14 into and through longitudinal slotted opening 26, so as to aid in the deployment, i.e., expelling, of implant device 14 from longitudinal slotted opening 26 of cannula 18-1 as stylet handle 16-2 of stylet assembly 16 is rotated relative to cannula handle 18-2 of cannula assembly 18.

Referring to FIGS. 2, 3, 7, and 8, in the present embodiment, implant device 14 may be made from a biocompatible memory material, e.g., a shape-memory polymer, or metal (e.g., nitinol). Also, implant device 14 may be made from a bioabsorbable material. Such a bioabsorbable material may be, for example, polyglycolic acid (PGA) or polylactic acid (PLA), or a combination (PLA-PGA).

Figure 8:
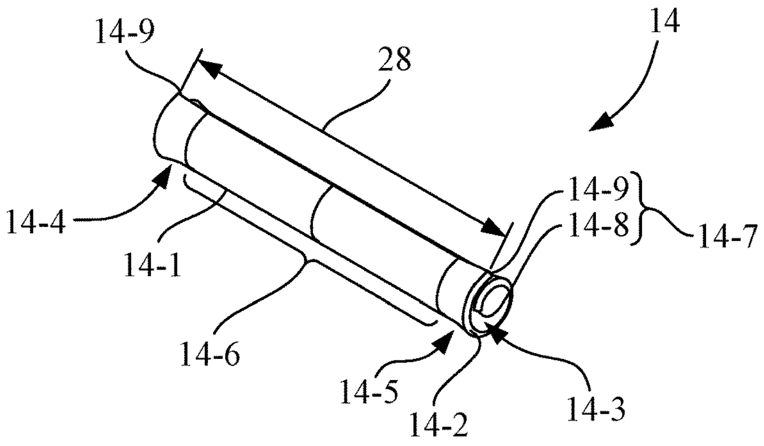
FIG. 8 is an enlarged view of the implant device of FIG. 1, with the implant device being in the form of an implantable tube.
Figure 9:
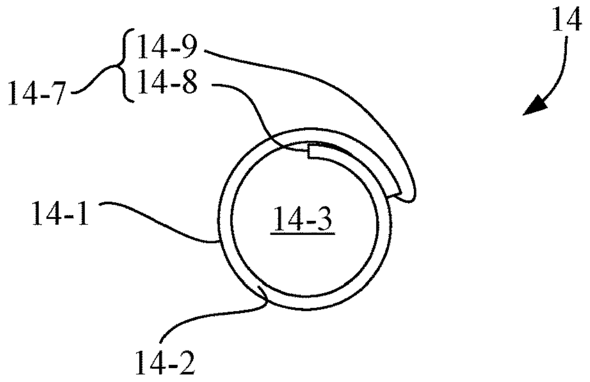
FIG. 9 is an end view of the implantable tube of FIG. 8, showing the leading and trailing lateral edge surfaces of the implantable tube.

Referring to FIGS. 8 and 9, in the present embodiment, implant device 14 is in the form of a rolled tube 14-1, formed as a single-piece structure. Tube 14-1 includes a tubular side wall 14-2, a tubular lumen 14-3, a proximal end portion 14-4, a distal end portion 14-5, and a central portion 14-6. Central portion 14-6 is interposed between proximal end portion 14-4 and distal end portion 14-5. Implant device 14 has a longitudinal extent 28, wherein each of proximal end portion 14-4 and distal end portion 14-5 extends outwardly, i.e., radially, from the central portion 14-6.

In the present embodiment, each of proximal end portion 14-4 and distal end portion 14-5 flares outwardly from central portion 14-6. Also, in the present embodiment, proximal end portion 14-4 and distal end portion 14-5 are symmetrical, on opposite ends of central portion 14-6.

Tubular side wall 14-2 has a longitudinal split 14-7 to define a first lateral edge surface 14-8 and a second lateral edge surface 14-9. Each of first lateral edge surface 14-8 and second lateral edge surface 14-9 longitudinally extends through each of the proximal end portion 14-4, the central portion 14-6, and the distal end portion 14-5. Also, each of first lateral edge surface 14-8 and second lateral edge surface 14-9 form a circumferential termination end surface of implant device 14.

Implant device 14, in the form of rolled tube 14-1, is shaped as a roll that overlaps on itself, wherein one of first lateral edge surface 14-8 and second lateral edge surface 14-9 is positioned on an exterior of implant device 14 and the other of first lateral edge surface 14-8 and second lateral edge surface 14-9 is positioned in an interior of implant device 14, depending on the direction of the roll. In the present embodiment, implant device 14 is shaped as a roll that overlaps on itself, wherein first lateral edge surface 14-8 is positioned in the interior, i.e., at tubular lumen 14-3, of implant device 14, and second lateral edge surface 14-9 is positioned at an exterior of implant device 14.

Referring again to FIGS. 1-4, and 10, stylet assembly 16 and cannula assembly 18 are arranged along a longitudinal axis 20, and the stylet assembly 16 and cannula assembly 18 are configured to rotate relative to each other to deploy the implant device 14 through longitudinal slotted opening 26 of cannula side wall 18-5. For example, in the present embodiment, stylet handle 16-2 is rotated in a rotational direction 30 relative to cannula handle 18-2, e.g., while cannula handle 18-2 is held stationary, or rotated in an opposite direction.

Figure 2:
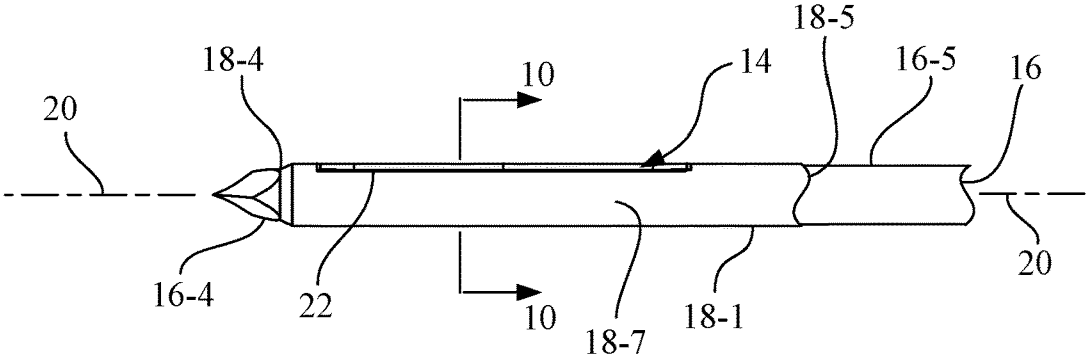
FIG. 2 is an enlarged view of the implant system of FIG. 1 in the pre-deployment state, with the implant device being in the form of an implantable tube partially visible through a longitudinal slotted opening in the cannula of the implant introducer device.

Referring to FIGS. 1 and 2, in a pre-deployment state, a substantial portion, e.g., 95 to 100 percent, of implant device 14, and a longitudinal portion of stylet 16-1 that includes longitudinal recess 16-6 of the stylet assembly 16, are received in cannula lumen 18-6 of cannula 18-1 of cannula assembly 18. Also referring to FIG. 10, in the pre-deployment state, tubular lumen 14-3 of implant device 14 is received over outwardly spiral surface portion 24 of exterior surface 16-5 of the stylet 16-1 of stylet assembly 16, with first lateral edge surface 14-8 of the tubular side wall 14-2 of the implant device 14 positioned to be engaged by longitudinal edge surface 22 of longitudinal recess 16-6 of stylet assembly 16.

Figure 10:
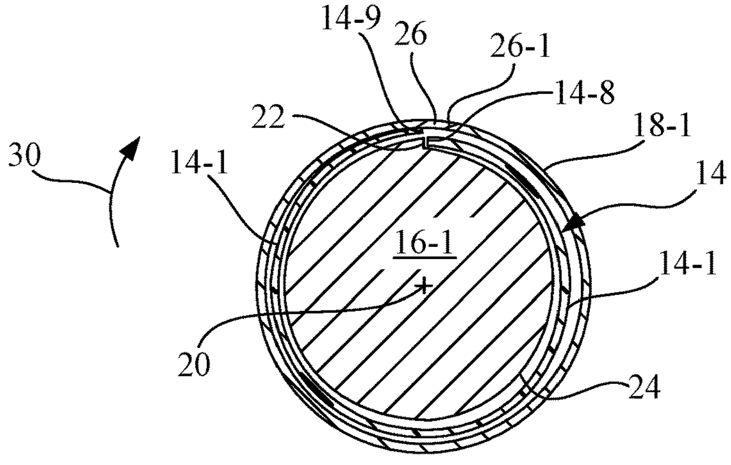
FIG. 10 is a further enlarged section view of the implant introducer device of FIG. 1, taken along line 10-10 of FIG. 2.
Figure 11:
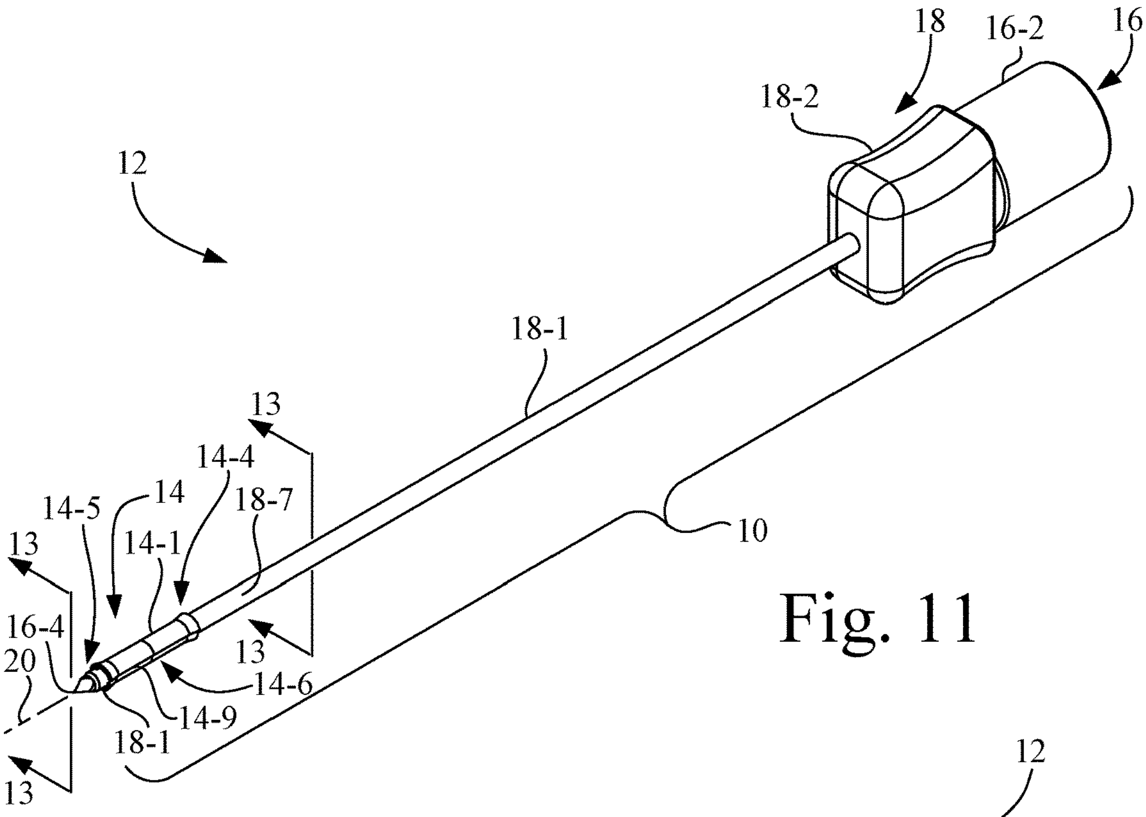
FIG. 11 is a perspective view of the implant system of FIG. 1 in a post-deployment state, which shows the implant device as an implantable tube positioned over an outer surface of the cannula of the implant introducer device, following ejection of the implantable tube from the longitudinal slotted opening of the cannula.
Figure 12:
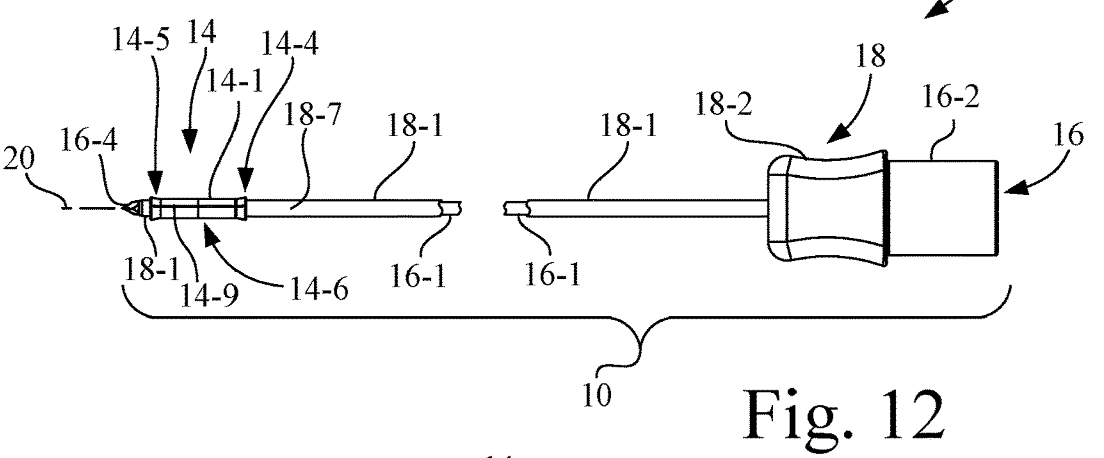
FIG. 12 is a side view of the implant system of FIG. 11.
Figure 13:
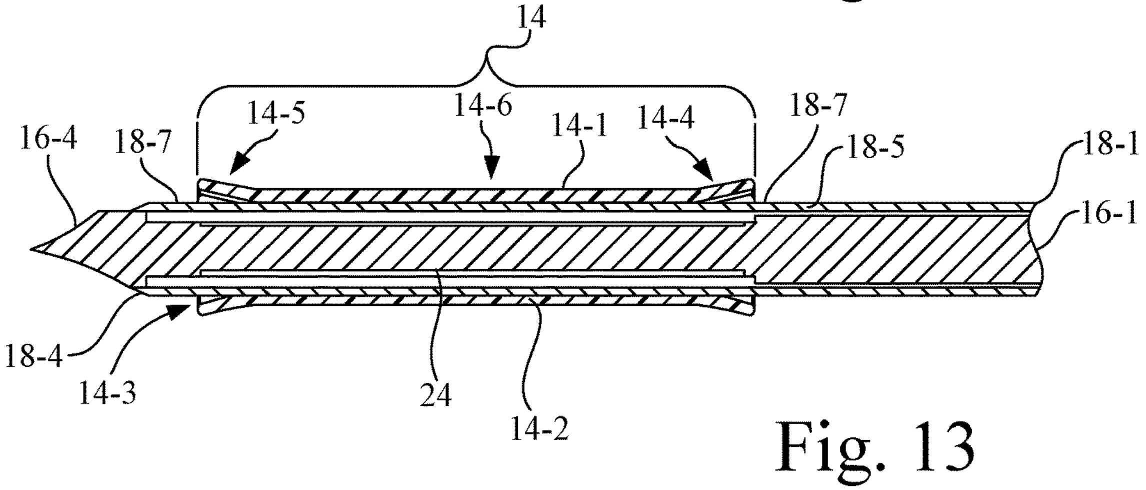
FIG. 13 is a section view of a portion of the implant introducer device and implantable tube of FIGS. 11 and 12, taken along plane 13-13-13-13 of FIG. 11.

As shown in FIG. 10, second lateral edge surface 14-9 of the tubular side wall 14-2 of the implant device 14 is positioned to be received through longitudinal slotted opening 26 of the cannula side wall 18-5. FIG. 3 shows implant device 14 during deployment, wherein a portion of rolled tube 14-1 has been extended through longitudinal slotted opening 26 (see also FIGS. 2, 4, and 7 for reference) of cannula 18-1.

Referring to FIGS. 1-4, 6, and 8-10, as stylet handle 16-2 is rotated in rotational direction 30 relative to cannula handle 18-2, e.g., while cannula handle 18-2 is held stationary or rotated in the opposite direction, longitudinal edge surface 22 of longitudinal recess 16-6 of stylet assembly 16 engages first lateral edge surface 14-8 of the tubular side wall 14-2 of the implant device 14, to in turn rotate implant device 14 about longitudinal axis 20. As implant device 14 is rotated, ramp 26-1 of longitudinal slotted opening 26 guides second lateral edge surface 14-9 of the tubular side wall 14-2 of the implant device 14 into and through longitudinal slotted opening 26 of cannula 18-1 of cannula assembly 18, to achieve the partially deployed state as depicted in FIG. 3.

FIGS. 11-14 show implant device 14 as being fully deployed, wherein implant device 14 is fully expelled from longitudinal slotted opening 26 of cannula 18-1 of cannula assembly 18. Referring again also to FIGS. 8-10, implant device 14 is fully deployed when first lateral edge surface 14-8 of tubular side wall 14-2 of implant device 14 exits longitudinal slotted opening 26 of cannula side wall 18-5 of cannula 18-1. As such, when implant device 14 is fully deployed, as depicted in FIGS. 11-14, cannula 18-1 is positioned in tubular lumen 14-3 of implant device 14, with implant device 14 surrounding a circumference around outer surface 18-7 of cannula 18-1 of cannula assembly 18.

In accordance with the present embodiment, a diameter of implant device 14 when entirely contained in cannula lumen 18-6 of the cannula 18-1 (pre-deployment; see, e.g., FIG. 10) is smaller than the diameter of implant device 14 when fully deployed and external to the cannula 18-1 (see FIGS. 11-14).

Figure 14:
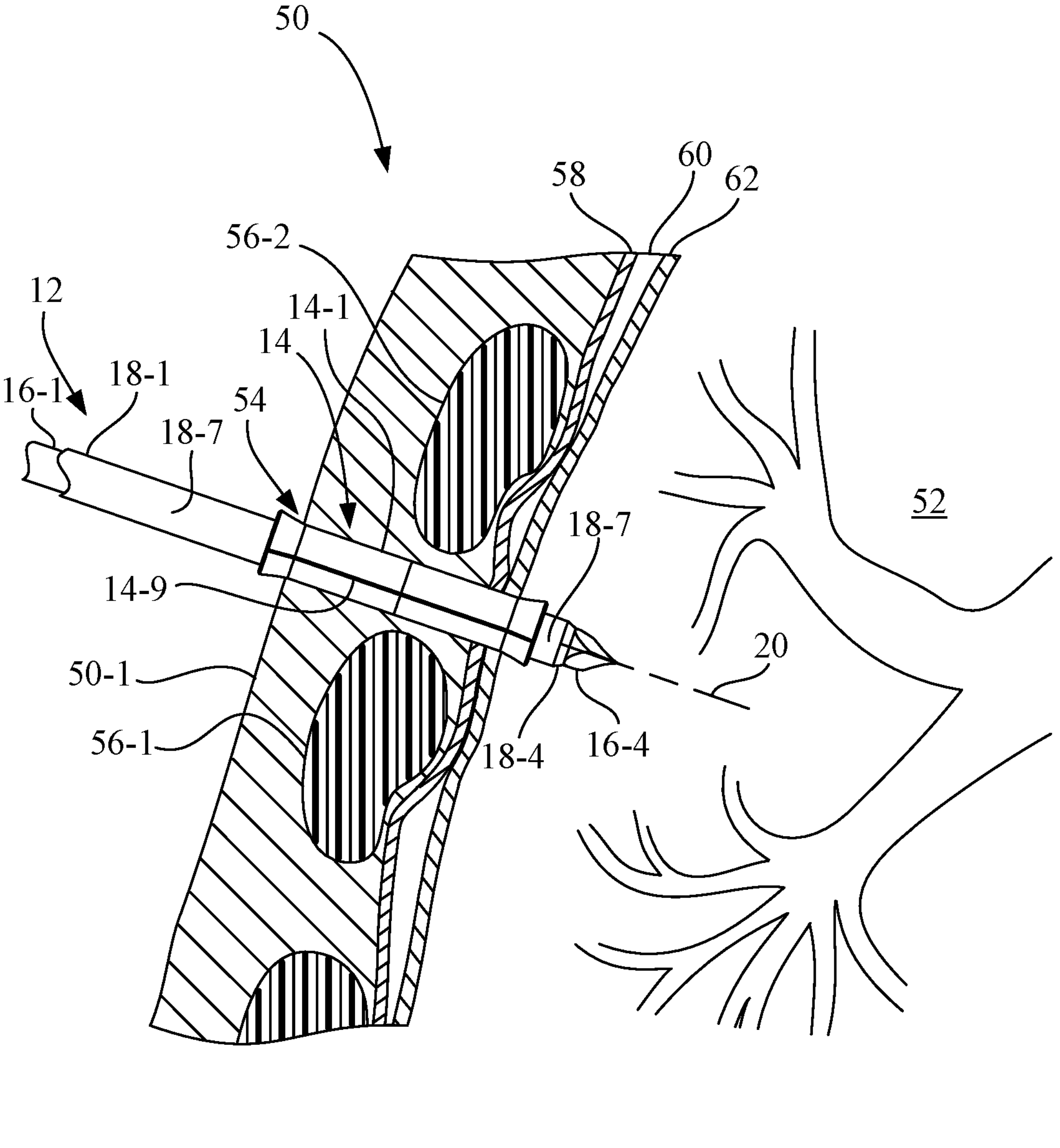
FIG. 14 is a pictorial representation of a portion of a chest wall and lung in cross-section, and with the implant system of FIGS. 11-13 in the post-deployment state with the implantable tube and implant introducer device positioned in an access opening in the chest wall and pleura layers.

FIG. 14 depicts a portion of a chest wall 50 and lung 52 of a patient. Implant introducer device 12 of implant system 10 (carrying implant device 14) is used to form an access opening 54 to the interior of lung 52. In particular, access opening 54 is formed between adjacent ribs 56-1, 56-2 in the rib cage of chest wall 50, and extends though the parietal pleura 58, the pleural space 60, and the visceral pleura 62 to provide access to the interior of lung 52. Once implant introducer device 12 of implant system 10 enters into the lung parenchyma, implant device 14 is moved from the cannula lumen 18-6 of cannula 18-1, through longitudinal slotted opening 26 of cannula 18-1, and to the fully deployed state by the rotation of stylet handle 16-2 relative to cannula handle 18-2. In FIG. 14, implant device 14 is shown positioned in access opening 54 in the fully deployed state (see also FIGS. 11-13), with implant device 14 spanning the tissue from the patient's skin 50-1 to below the visceral pleura 62.

A lung access procedure, such as a lung biopsy, may be carried out by removing stylet 16-1 of stylet assembly 16 from cannula assembly 18 of implant introducer device 12, and then inserting a lung biopsy device through cannula lumen 18-6 of cannula 18-1 of cannula assembly 18 and into the lung. Alternatively, the lung access procedure may be carried out by removing the entirety of implant introducer device 12 from tubular lumen 14-3 of implant device 14, and a lung biopsy device may be inserted through tubular lumen 14-3 of implant device 14 and into the lung.

Referring to FIGS. 15A-15E, there is shown an implant device 100 in accordance with another embodiment. For convenience, implant device 100 is shown oriented on a longitudinal axis 102.

Implant device 100 is formed as an implant tube 100-1, which may be made from a biocompatible material, such as a biocompatible polymer. Also, implant tube 100-1 may be made from a bioabsorbable material. Such a bioabsorbable material may be, for example, polyglycolic acid (PGA) or polylactic acid (PLA), or a combination (PLA-PGA). Further, implant tube 100-1 may be made from a shape-memory polymer.

Implant tube 100-1 is in the form of a single-piece structure, and includes a tubular side wall 100-2, a tubular lumen 100-3, a proximal end portion 100-4, a distal end portion 100-5, and a central portion 100-6. Central portion 100-6 is interposed between proximal end portion 100-4 and distal end portion 100-5. Implant tube 100-1 has a longitudinal extent 104, wherein each of proximal end portion 100-4 and distal end portion 100-5 extends outwardly, i.e., radially, from the central portion 100-6.

In the present embodiment, each of proximal end portion 100-4 and distal end portion 100-5 flares outwardly from central portion 100-6. Also, in the present embodiment, proximal end portion 100-4 and distal end portion 100-5 are symmetrical, on opposite ends of central portion 100-6. Further, referring to FIGS. 15B and 15D, in the present embodiment, each of proximal end portion 100-4, distal end portion 100-5, and central portion 100-6 may have a substantially planar exterior surface profile. Also, tubular side wall 100-2 may have substantially the same wall thickness across proximal end portion 100-4, distal end portion 100-5, and central portion 100-6.

Tubular side wall 100-2 has a longitudinal split 100-7 to define a first lateral edge surface 100-8 and a second lateral edge surface 100-9. Each of first lateral edge surface 100-8 and second lateral edge surface 100-9 form a circumferential termination end surface of implant tube 100-1. In the present embodiment, first lateral edge surface 100-8 and the second lateral edge surface 100-9 are spaced apart to define a longitudinal gap 106 between the first lateral edge surface 100-8 and the second lateral edge surface 100-9, wherein the longitudinal gap 106 longitudinally extends through each of the proximal end portion 100-4, the central portion 100-6, and the distal end portion 100-5. Likewise, each of first lateral edge surface 100-8 and second lateral edge surface 100-9 longitudinally extends through each of the proximal end portion 100-4, the central portion 100-6, and the distal end portion 100-5.

Figure 15A:
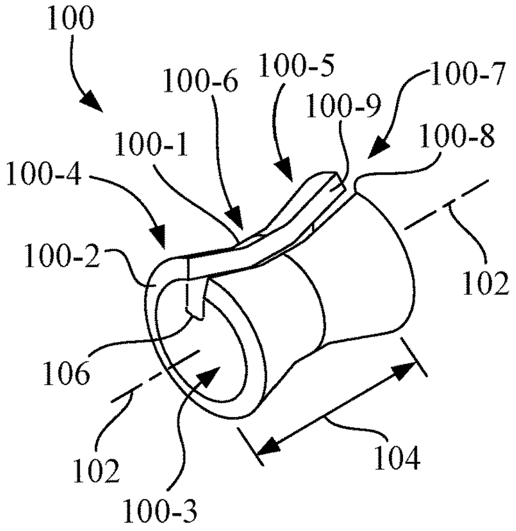
FIG. 15A is a perspective view of an implant device in accordance with another embodiment, showing a longitudinal gap between the lateral edge surfaces of the implant device.
Figure 15B:
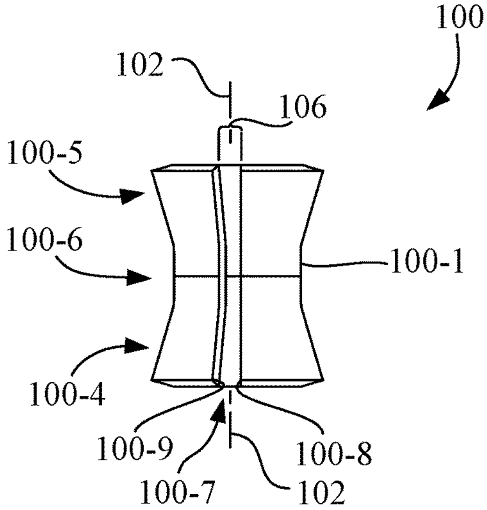
FIG. 15B is a side view of the implant device of FIG. 15A, showing the longitudinal gap between the lateral edge surfaces of the implant device.
Figure 15C:
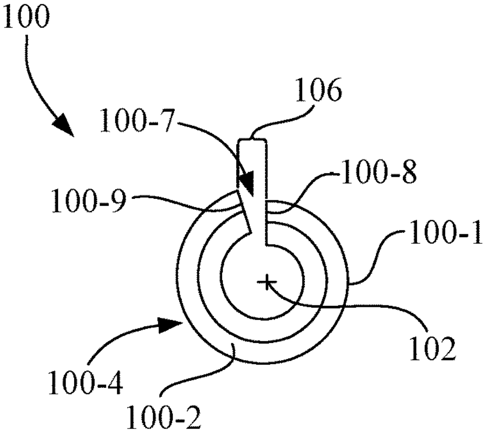
FIG. 15C is an end view of the implant device of FIGS. 15A and 15B, showing the radial offset of the lateral edge surfaces across the longitudinal gap of the implant device.
Figure 15D:
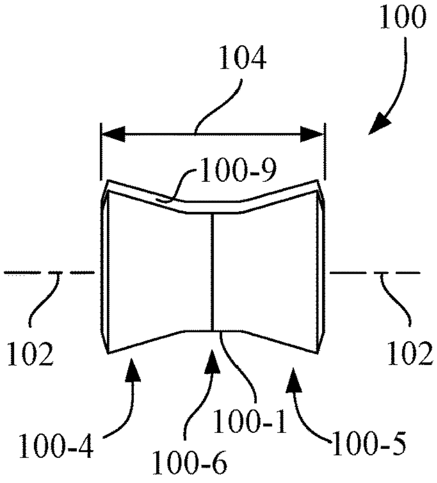
FIG. 15D is a side view of the implant device of FIGS. 15A and 15B, showing the radial offset of the lateral edge surfaces of the implant device.

In the present embodiment, implant tube 100-1 is shaped such that first lateral edge surface 100-8 and second lateral edge surface 100-9 face one another across longitudinal gap 106. However, as best shown in FIG. 15C, while first lateral edge surface 100-8 and second lateral edge surface 100-9 face one another across longitudinal gap 106, first lateral edge surface 100-8 and second lateral edge surface 100-9 are radially offset from one another, and have different radial spacings from longitudinal axis 102.

Figure 15E:
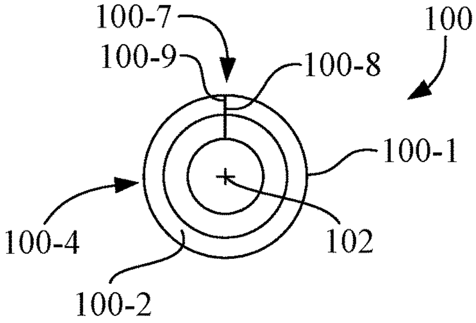
FIG. 15E is an end view of the implant device of FIGS. 15A and 15B, showing the longitudinal gap between the lateral edge surfaces of the implant device being closed, as when the implant device is acted upon by external forces.

Referring to FIG. 15E, following deployment of implant device 100 in an access opening, such as access opening 54 (see, e.g., FIG. 14) of a patient, longitudinal gap 106 is closed by the radial compressive force exerted by the tissue that surrounds access opening 54. A lung access procedure may be carried out through tubular lumen 100-3 of implant tube 100-1, wherein a lung biopsy device (with or without a guide cannula) may be inserted through tubular lumen 100-3 of implant tube 100-1 and into the lung.

Referring to FIGS. 16A-16D, there is shown an implant device 120 in accordance with another embodiment. For convenience, implant device 120 is shown oriented on a longitudinal axis 122.

Implant device 120 is formed as an implant tube 120-1, which may be made from a biocompatible material, such as a biocompatible polymer. Also, implant tube 120-1 may be made from a bioabsorbable material. Such a bioabsorbable material may be, for example, polyglycolic acid (PGA) or polylactic acid (PLA), or a combination (PLA-PGA). Further, implant tube 120-1 may be made from a shape-memory polymer.

Implant tube 120-1 is in the form of a single-piece structure, and includes a tubular side wall 120-2, a tubular lumen 120-3, a proximal end portion 120-4, a distal end portion 120-5, and a central portion 120-6. Central portion 120-6 is interposed between proximal end portion 120-4 and distal end portion 120-5. Implant tube 120-1 has a longitudinal extent 124, wherein each of proximal end portion 120-4 and distal end portion 120-5 extends outwardly, i.e., radially, from the central portion 120-6.

In the present embodiment, each of proximal end portion 120-4 and distal end portion 120-5 flares outwardly from central portion 120-6. Each of the proximal end portion 120-4 and the distal end portion 120-5 includes a respective plurality of finger members 126-1, 126-2 that are spaced around a periphery of each of proximal end portion 120-4 and distal end portion 120-5. The plurality of finger members 126-1, 126-2 may extend, e.g., both longitudinally and radially, from at least one of the proximal end portion 120-4 and distal end portion 120-5. When implant device 120 is deployed, the plurality of finger members 126-1, 126-2 may serve as anchors to resist migration of implant device 120 along an access opening, such as access opening 54 (see, e.g., FIG. 14) of a patient.

Each of the plurality of finger members 126-1, 126-2 may be formed integral with proximal end portion 120-4 and the distal end portion 120-5 during a polymer molding process. Alternatively, for example, each of the plurality of finger members 126-1, 126-2 may be formed by removing material from proximal end portion 120-4 and the distal end portion 120-5. It is further contemplated that in some implementations, only one of proximal end portion 120-4 and the distal end portion 120-5 may include the plurality of finger members.

In the present embodiment, proximal end portion 120-4 and distal end portion 120-5 are symmetrical, on opposite ends of central portion 120-6. Further, in the present embodiment, each of proximal end portion 120-4, distal end portion 120-5, and central portion 120-6 has a substantially planar exterior surface profile, as shown for example, in FIGS. 16B and 16D, and tubular side wall 120-2 may have substantially the same wall thickness across proximal end portion 120-4, distal end portion 120-5, and central portion 120-6.

Tubular side wall 120-2 has a longitudinal split 120-7 to define a first lateral edge surface 120-8 and a second lateral edge surface 120-9. Each of first lateral edge surface 120-8 and second lateral edge surface 120-9 form a circumferential termination end surface of implant tube 120-1. In the present embodiment, first lateral edge surface 120-8 and the second lateral edge surface 120-9 are spaced apart to define a longitudinal gap 128 between the first lateral edge surface 120-8 and the second lateral edge surface 120-9, wherein the longitudinal gap 128 longitudinally extends through each of the proximal end portion 120-4, the central portion 120-6, and the distal end portion 120-5. Likewise, each of first lateral edge surface 120-8 and second lateral edge surface 120-9 longitudinally extends through each of the proximal end portion 120-4, the central portion 120-6, and the distal end portion 120-5.

Figure 16A:
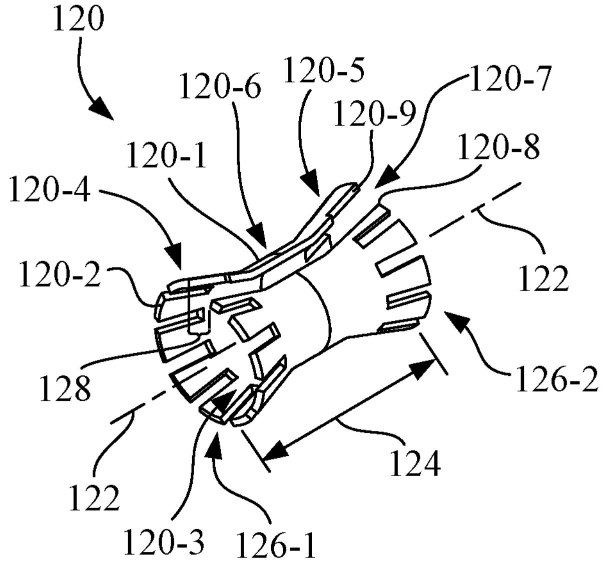
FIG. 16A is a perspective view of an implant device in accordance with another embodiment, showing a longitudinal gap between the lateral edge surfaces of the implant device.
Figure 16B:
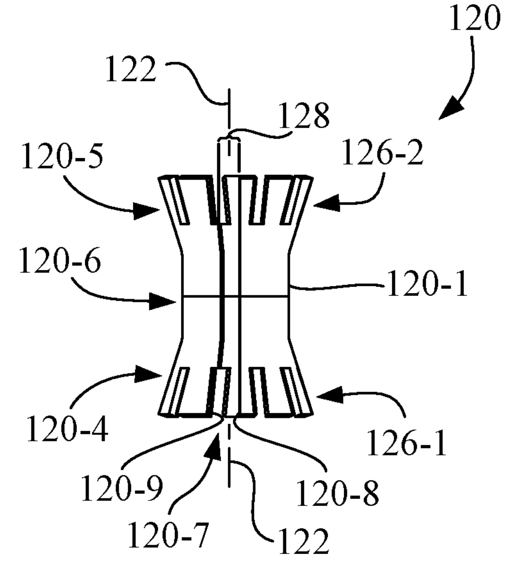
FIG. 16B is a side view of the implant device of FIG. 16A, showing the longitudinal gap between the lateral edge surfaces of the implant device.
Figure 16C:
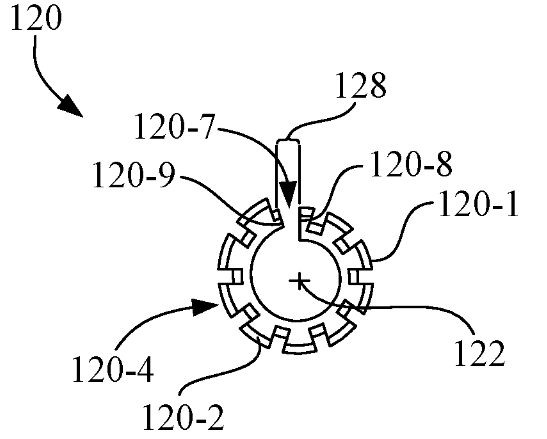
FIG. 16C is an end view of the implant device of FIGS. 16A and 16B, showing the radial offset of the lateral edge surfaces across the longitudinal gap of the implant device.
Figure 16D:
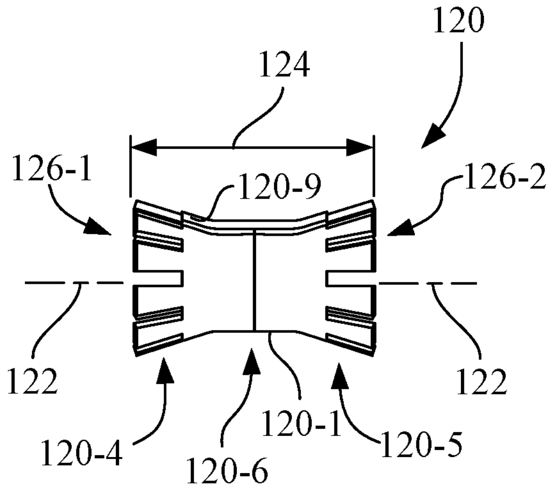
FIG. 16D is a side view of the implant device of FIGS. 16A and 16B, showing the radial offset of the lateral edge surfaces of the implant device.

In the present embodiment, implant tube 120-1 is shaped such that first lateral edge surface 120-8 and second lateral edge surface 120-9 face one another across longitudinal gap 128. However, as best shown in FIG. 16C, while first lateral edge surface 120-8 and second lateral edge surface 120-9 face one another across longitudinal gap 128, first lateral edge surface 120-8 and second lateral edge surface 120-9 are radially offset from one another, and have different radial spacings from longitudinal axis 122.

Following deployment of implant device 120 in an access opening, such as access opening 54 (see, e.g., FIG. 14) of a patient, longitudinal gap 128 is closed by the radial compressive force exerted by the tissue that surrounds access opening 54. A lung access procedure may be carried out through tubular lumen 120-3 of implant tube 120-1, wherein a lung biopsy device (with or without a guide cannula) may be inserted through tubular lumen 120-3 of implant tube 120-1 and into the lung.

Referring to FIGS. 17A-17D, there is shown an implant device 140 in accordance with another embodiment. For convenience, implant device 140 is shown oriented on a longitudinal axis 142.

Implant device 140 is formed as an implant tube 140-1, which may be made from a biocompatible material, such as a biocompatible polymer. Also, implant tube 140-1 may be made from a bioabsorbable material. Such a bioabsorbable material may be, for example, polyglycolic acid (PGA) or polylactic acid (PLA), or a combination (PLA-PGA). Further, implant tube 140-1 may be made from a shape-memory polymer.

Implant tube 140-1 is a single-piece structure, and includes a tubular side wall 140-2, a tubular lumen 140-3, a proximal end portion 140-4, a distal end portion 140-5, and a central portion 140-6. Central portion 140-6 is interposed between proximal end portion 140-4 and distal end portion 140-5. Implant tube 140-1 has a longitudinal extent 144, wherein each of proximal end portion 140-4 and distal end portion 140-5 extends outwardly, i.e., radially, from the central portion 140-6.

In the present embodiment, each of proximal end portion 140-4 and distal end portion 140-5 flares outwardly from central portion 140-6. Also, in the present embodiment, proximal end portion 140-4 and distal end portion 140-5 are symmetrical, on opposite ends of central portion 140-6.

For example, in the present embodiment, each of the proximal end portion 140-4 and the distal end portion 140-5 includes a respective enlarged annular portion 146-1, 146-2. Each of enlarged annular portion 146-1 and enlarged annular portion 146-2 has a greater outer diameter than the outer diameter of central portion 140-6. Each of the enlarged annular portion 146-1, 146-2 has a curved exterior surface and has a longitudinal radius that extends from tubular lumen 140-3 around a thickness of tubular side wall 140-2 at central portion 140-6 at respective proximal end portion 140-4 and distal end portion 140-5. When implant device 140 is deployed, each enlarged annular portion 146-1, 146-2 may serve as an anchor to resist migration of implant device 140 along an access opening, such as access opening 54 (see, e.g., FIG. 14) of a patient.

Tubular side wall 140-2 has a longitudinal split 140-7 to define a first lateral edge surface 140-8 and a second lateral edge surface 140-9. Each of first lateral edge surface 140-8 and second lateral edge surface 140-9 form a circumferential termination end surface of implant tube 140-1. In the present embodiment, first lateral edge surface 140-8 and the second lateral edge surface 140-9 are spaced apart to define a longitudinal gap 148 between the first lateral edge surface 140-8 and the second lateral edge surface 140-9, wherein the longitudinal gap 148 longitudinally extends through each of the proximal end portion 140-4, the central portion 140-6, and the distal end portion 140-5. Likewise, each of first lateral edge surface 140-8 and second lateral edge surface 140-9 longitudinally extends through each of the proximal end portion 140-4, the central portion 140-6, and the distal end portion 140-5.

Figure 17A:
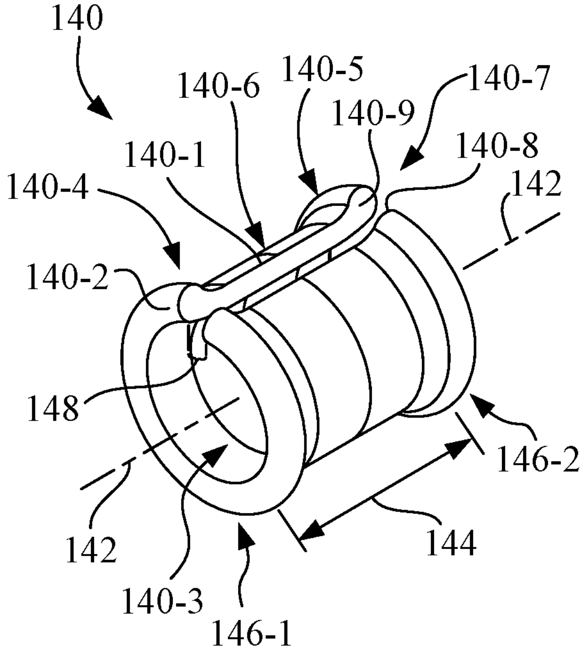
FIG. 17A is a perspective view of an implant device in accordance with another embodiment, showing a longitudinal gap between the lateral edge surfaces of the implant device.
Figure 17B:
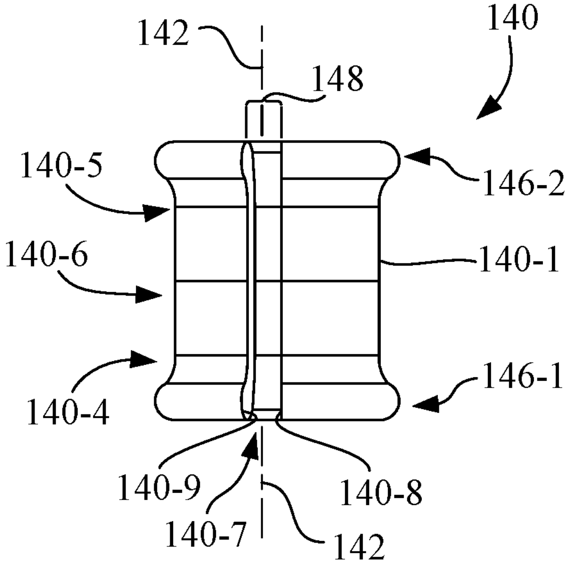
FIG. 17B is a side view of the implant device of FIG. 17A, showing the longitudinal gap between the lateral edge surfaces of the implant device.
Figure 17C:
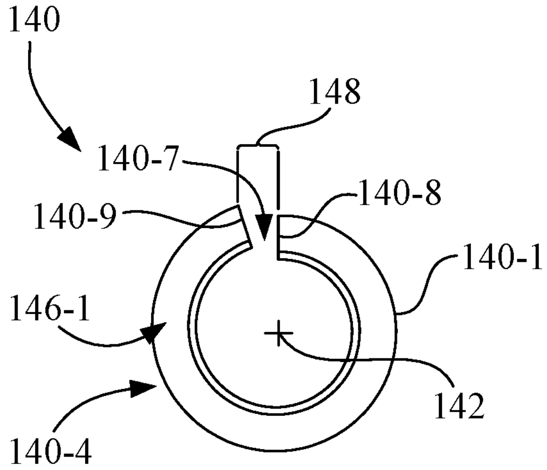
FIG. 17C is an end view of the implant device of FIGS. 17A and 176B, showing the radial offset of the lateral edge surfaces across the longitudinal gap of the implant device.
Figure 17D:
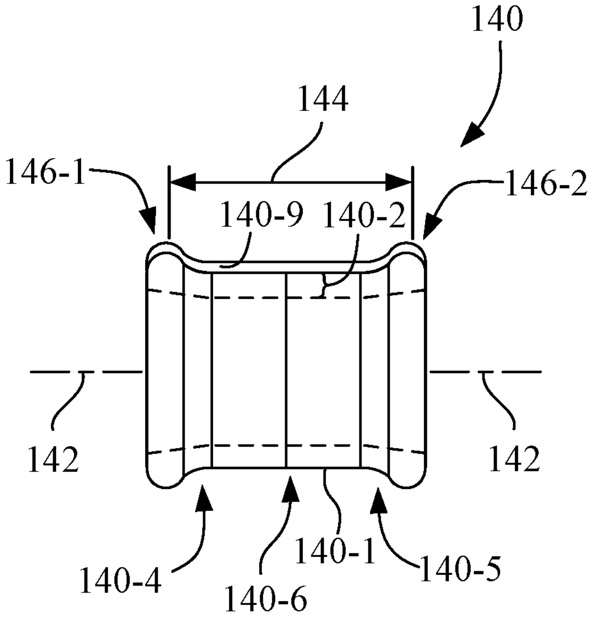
FIG. 17D is a side view of the implant device of FIGS. 17A and 17B, showing the radial offset of the lateral edge surfaces of the implant device.

In the present embodiment, implant tube 140-1 is shaped such that first lateral edge surface 140-8 and second lateral edge surface 140-9 face one another across longitudinal gap 148. However, as best shown in FIG. 17C, while first lateral edge surface 140-8 and second lateral edge surface 140-9 face one another across longitudinal gap 148, first lateral edge surface 140-8 and second lateral edge surface 140-9 are radially offset from one another, and have different radial spacings from longitudinal axis 142.

Following deployment of implant device 140 in an access opening, such as access opening 54 (see, e.g., FIG. 14) of a patient, longitudinal gap 148 is closed by the radial compressive force exerted by the tissue that surrounds access opening 54. A lung access procedure may be carried out through tubular lumen 140-3 of implant tube 140-1, wherein a lung biopsy device (with or without a guide cannula) may be inserted through tubular lumen 140-3 of implant tube 140-1 and into the lung.

The following items also relate to the invention:

In one form, the invention relates to an implant device to facilitate access across pleura layers. The implant device includes a tube having a side wall, a lumen, a proximal end portion, a distal end portion, and a central portion interposed between the proximal end portion and the distal end portion. The tube has a longitudinal extent. Each of the proximal end portion and the distal end portion extends outwardly from the central portion. The side wall has a longitudinal split to define a first lateral edge surface and a second lateral edge surface, wherein each of the first lateral edge surface and the second lateral edge surface longitudinally extends through each of the proximal end portion, the central portion, and the distal end portion.

In some embodiments, the first lateral edge surface and the second lateral edge surface may be spaced apart to define a longitudinal gap between the first lateral edge surface and the second lateral edge surface, wherein the longitudinal gap may longitudinally extend through each of the proximal end portion, the central portion, and the distal end portion.

In some other embodiments, the tube may be shaped as a roll that overlaps on itself, wherein one of the first lateral edge surface and the second lateral edge surface may be positioned on an exterior of the tube and the other of the first lateral edge surface and the second lateral edge surface may be positioned in an interior of the tube.

In any of the embodiments, each of the proximal end portion and the distal end portion optionally may flare outwardly from the central portion.

In any of the embodiments, the proximal end portion and the distal end portion optionally may be symmetrical, on opposite ends of the central portion.

In at least one embodiment, a plurality of finger members optionally may extend from at least one of the proximal end portion and the distal end portion.

In at least one embodiment, each of the proximal end portion and the distal end portion optionally may include a respective plurality of finger members that are spaced around a periphery of each of the proximal end portion and the distal end portion.

In any of the embodiments, the implant may be made from a memory material.

In any of the embodiments, the implant may be made from a bioabsorbable material.

In any of the embodiments, the implant may be made from one of a metal or a polymer.

In another form, the invention relates to a system to facilitate access across pleura layers. The system includes an implantable tube having a tubular side wall, a tubular lumen, a proximal end portion, a distal end portion, and a central portion interposed between the proximal end portion and the distal end portion. The implantable tube has a longitudinal extent, wherein each of the proximal end portion and the distal end portion extends outwardly from the central portion. The tubular side wall has a longitudinal split to define a first lateral edge surface and a second lateral edge surface, wherein each of the first lateral edge surface and the second lateral edge surface longitudinally extends through each of the proximal end portion, the central portion, and the distal end portion. The system may include a stylet assembly having a stylet and a stylet handle. The stylet has a distal tip. The stylet has an exterior surface and a longitudinal recess formed along the exterior surface of the stylet. The longitudinal recess has a longitudinal edge surface. The tubular lumen of the implantable tube may be configured to be received over the exterior surface of the stylet, with the first lateral edge surface of the tubular side wall of the implantable tube configured to be engaged by the longitudinal edge surface of the longitudinal recess of the stylet. The system may include a cannula assembly having a cannula and a cannula handle. The cannula has a cannula side wall and a cannula lumen. The cannula side wall has a distal end and a longitudinal slotted opening proximal to the distal end. The implantable tube and at least a portion of the stylet may be configured to be received in the cannula lumen, with the second lateral edge surface of the tubular side wall of the implantable tube configured to be received through the longitudinal slotted opening of the cannula side wall.

In any of the embodiments of the system above, the stylet and cannula may be arranged along a longitudinal axis, and the stylet and cannula may be configured to rotate relative to each other to deploy the implantable tube through the longitudinal slotted opening of the cannula side wall.

In any of the embodiments of the system above, the implantable tube may be fully deployed when the first lateral edge surface of the tubular side wall of the implantable tube exits the longitudinal slotted opening of the cannula side wall.

In any of the embodiments of the system above, when the implantable tube is fully deployed, the cannula may be positioned in the tubular lumen of the implantable tube.

In at least some of the embodiments of the system above, the longitudinal slotted opening may include a ramp that extends from the cannula lumen to an outer surface of the cannula. The ramp may be configured to guide the second lateral edge surface of the tubular side wall of the implantable tube into and through the longitudinal slotted opening.

In any of the embodiments of the system above, a diameter of the implantable tube when contained in the cannula lumen of the cannula may be smaller than the diameter of the implantable tube when fully deployed and external to the cannula.

In any of the embodiments of the system above, the implantable tube may be shaped as a roll that overlaps on itself, wherein the first lateral edge surface may be positioned in an interior of the implantable tube and the second lateral edge surface may be positioned on an exterior of the implantable tube.

In any of the embodiments of the system above, each of the proximal end portion and the distal end portion optionally may flare outwardly from the central portion.

In any the embodiments of the system above, the proximal end portion and the distal end portion optionally may be symmetrical, on opposite ends of the central portion.

In any of the embodiments of the system above, the implantable tube may be made from a memory material.

As used herein, "substantial", "substantially," and other words of degree are relative modifiers intended to indicate permissible variation from the characteristic so modified. It is not intended to be limited to the absolute value or characteristic which it modifies, but rather, possessing more of the physical or functional characteristic than its opposite, and approaching or approximating such a physical or functional characteristic.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An implant device to facilitate access across pleura layers via an access opening through at least the pleura layers, the implant device comprising:

a tube having a side wall, a lumen, a proximal end portion, a distal end portion, and a central portion interposed between the proximal end portion and the distal end portion, the tube having a longitudinal extent and defining a longitudinal axis, wherein each of the proximal end portion and the distal end portion extends outwardly from the central portion, wherein, in an undeployed state, the side wall has a longitudinal split extending the longitudinal extent and defining a first lateral edge surface facing a second lateral edge surface across a longitudinal gap therebetween, the first lateral edge surface having a first radial spacing from the longitudinal axis and the second lateral edge surface having a second radial spacing from the longitudinal axis that is different from the first radial spacing so that the first lateral edge surface and the second lateral edge surface are radially offset with respect to one another, and wherein, in a deployed state when the tube is arranged within the access opening, the longitudinal gap is closed so the first lateral edge surface contacts the second lateral edge surface and the first radial spacing is the same as the second radial spacing.

2. The implant device according to claim 1, wherein each of the first lateral edge surface and the second lateral edge surface is configured to form a circumferential termination end surface of the implant device.

3. The implant device according to claim 1, wherein each of the proximal end portion and the distal end portion flares outwardly from the central portion.

4. The implant device according to claim 3, wherein the proximal end portion, the distal end portion, and the central portion each have a planar exterior surface profile.

5. The implant device according to claim 3, wherein the side wall has a constant thickness in the proximal end portion, the distal end portion, and the central portion.

6. The implant device according to claim 1, wherein the proximal end portion and the distal end portion are symmetrical, on opposite sides of the central portion.

7. The implant device according to claim 1, comprising a plurality of finger members that extend from at least one of the proximal end portion and the distal end portion.

8. The implant device according to claim 1, wherein each of the proximal end portion and the distal end portion includes a respective plurality of finger members that are spaced around a periphery of each of the proximal end portion and the distal end portion.

9. The implant device according to claim 1, wherein the implant device is formed of at least one of a memory material, a bioabsorbable material, a metal, or a polymer.

10. A system to facilitate access across pleura layers via an access opening through at least the pleura layers, the system comprising:

an implantable tube having a tubular side wall, a tubular lumen, a proximal end portion, a distal end portion, and a central portion interposed between the proximal end portion and the distal end portion, the implantable tube having a longitudinal extent and defining a longitudinal axis, wherein each of the proximal end portion and the distal end portion extends outwardly from the central portion, and wherein, in an undeployed state, the tubular side wall has a longitudinal split extending the longitudinal extent to define a first lateral edge surface facing a second lateral edge surface across a longitudinal gap therebetween, the first lateral edge surface having a first radial spacing from the longitudinal axis and the second lateral edge surface having a second radial spacing from the longitudinal axis that is different from the first radial spacing so that the first lateral edge surface and the second lateral edge surface are radially offset with respect to one another;

a stylet assembly having a stylet and a stylet handle, the stylet having a distal tip, the stylet having an exterior surface and a longitudinal recess formed along the exterior surface of the stylet, the longitudinal recess having a longitudinal edge surface, the tubular lumen of the implantable tube configured to be received over the exterior surface of the stylet, with the first lateral edge surface of the tubular side wall of the implantable tube configured to be engaged by the longitudinal edge surface of the longitudinal recess of the stylet;

and a cannula assembly having a cannula and a cannula handle, the cannula having a cannula side wall and a cannula lumen, the cannula side wall having a distal end and a longitudinal slotted opening proximal to the distal end, wherein the implantable tube and at least a portion of the stylet are configured to be received in the cannula lumen, with the second lateral edge surface of the tubular side wall of the implantable tube configured to be received through the longitudinal slotted opening of the cannula side wall, wherein, when the implantable tube is moved to a deployed state via the cannula assembly within the access opening, the longitudinal gap of the implantable tube is closed so that the first lateral edge surface of the implantable tube contacts the second lateral edge surface of the implantable tube and the first radial spacing is the same as the second radial spacing.

11. The system according to claim 10, wherein the stylet and the cannula are arranged along a longitudinal axis, and the stylet and the cannula are configured to rotate relative to each other to deploy the implantable tube through the longitudinal slotted opening of the cannula side wall to the deployed state.

12. The system according to claim 10, wherein the longitudinal slotted opening includes a ramp that extends from the cannula lumen to an outer surface of the cannula, the ramp configured to guide the second lateral edge surface of the tubular side wall of the implantable tube into and through the longitudinal slotted opening.

13. The system according to claim 10, wherein a diameter of the implantable tube when the implantable tube is in the undeployed state is smaller than the diameter of the implantable tube when the implantable tube is in the deployed state.

14. The system according to claim 10, wherein each of the proximal end portion and the distal end portion flares outwardly from the central portion.

15. The system according to claim 10, wherein the proximal end portion and the distal end portion are symmetrical, on opposite ends of the central portion.

16. The system according to claim 10, wherein the implantable tube is made from a memory material.

17. The system according to claim 10, wherein the implantable tube further comprises a plurality of finger members that extend from at least one of the proximal end portion and the distal end portion.

18. The system according to claim 10, wherein each of the proximal end portion and the distal end portion of the implantable tube includes a respective plurality of finger members that are spaced around a periphery of each of the proximal end portion and the distal end portion.

* * * * *